United States Patent [19]

Steiner et al.

[11] Patent Number: 5,753,690

[45] Date of Patent: May 19, 1998

[54] N-SUBSTITUTED AZOBICYCLOHEPTANE DERIVATIVES, THE PREPARATION AND USE THEREOF

[75] Inventors: Gerd Steiner, Kirchheim; Rainer Munschauer, Neustadt; Thomas Höger, Edingen-Neckarhausen; Liliane Unger, Ludwigshafen; Hans-Jürgen Teschendorf, Dudenhofen, all of Germany

[73] Assignee: BASF Aktiengesellschaft, Ludwigshafen, Germany

[21] Appl. No.: 776,583

[22] PCT Filed: Jul. 22, 1995

[86] PCT No.: PCT/EP95/02912

§ 371 Date: Feb. 3, 1997

§ 102(e) Date: Feb. 3, 1997

[87] PCT Pub. No.: WO96/04245

PCT Pub. Date: Feb. 15, 1996

[30] Foreign Application Priority Data

Aug. 4, 1994 [DE] Germany .............. 44 27 647.8

[51] Int. Cl.⁶ .............. A61K 31/40; C07D 209/56; C07D 209/02; C07D 209/44
[52] U.S. Cl. .............. 514/411; 514/412; 514/414; 514/421; 548/437; 548/455; 548/465; 548/515
[58] Field of Search .............. 548/437, 455, 548/465, 515; 514/411, 412, 414, 421

[56] References Cited

U.S. PATENT DOCUMENTS 5,475,105 12/1995 Steiner et al. .............. 544/48
5,521,209 5/1996 Steiner et al. .............. 514/112

FOREIGN PATENT DOCUMENTS 42 19 973 12/1993 Germany .
42 43 287 12/1993 Germany .
95/15312 6/1995 WIPO .

OTHER PUBLICATIONS

Specification and claims from BASF 0050/44494, N-substituted Azabicycloheptane Derivatives, Their Preparation and Use.

Primary Examiner—Mukund J. Shah
Assistant Examiner—Brenda Coleman
Attorney, Agent, or Firm—Keil & Weinkauf

[57] ABSTRACT

A compound of the formula

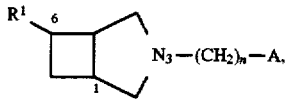

in which A, $R^1$ and n have the meanings stated in the description are described. The novel compounds are suitable for controlling diseases.

3 Claims, No Drawings

N-SUBSTITUTED AZOBICYCLOHEPTANE DERIVATIVES, THE PREPARATION AND USE THEREOF

BACKGROUND OF THE INVENTION

1. Field of the Invention

This application is a 371 of PCT/EP95/02912 filed Jul. 22, 1995.

The present invention relates to novel N-substituted azabicycloheptane derivatives, and to their preparation and use for the preparation of drugs.

2. Description of Related Art

It is known that N-substituted azabicycloheptane derivatives have surprising affinity for dopamine and serotinin receptor subtypes (DE 42 43 287, DE 42 19 973). The observed affinities for the $D_4$ dopamine receptor subtype play a special role in this.

SUMMARY OF THE INVENTION

We have now found that N-substituted 3-azabicyclo [3.2.0]-heptane derivatives of the formula I

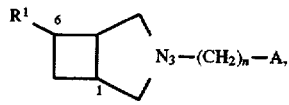

where $R^1$ is naphthyl or phenanthryl which is unsubstituted, mono- or di-substituted by halogen atoms, n is 1, 2, 3 or 4, A is

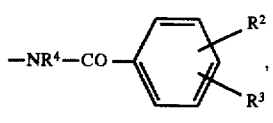

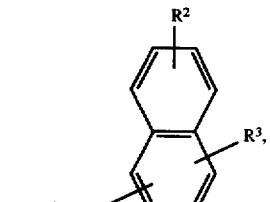

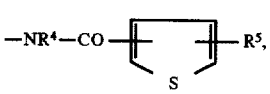

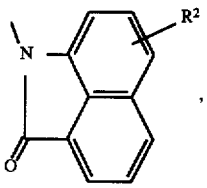

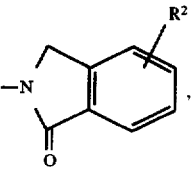

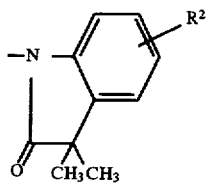

or naphthyl which is unsubstituted or halogen-substituted, $R^2$ is hydrogen, hydroxyl, $C_1$–$C_4$-alkyl, nitro or methoxy, or fluorine, chlorine, bromine or iodine, $R^3$ is hydrogen, fluorine or chlorine, $R^4$ is hydrogen or methyl, and $R^5$ is hydrogen or chlorine, and the salts thereof with physiologically tolerated acids, have valuable pharmacological properties.

DESCRIPTION OF PREFERRED EMBODIMENTS

The substituents $R^1$ to $R^5$, and n, in the formula I preferably have the following meanings:

$R^1$: naphthyl n: 2

$R^2$: hydrogen, hydroxyl, fluorine, chlorine, methylamino, amino $R^3$: hydrogen or chlorine $R^4$: hydrogen $R^5$: hydrogen or p-chloro The compounds of the formula I according to the invention can be prepared by reacting a compound of the formula II

  (II), where A and n have the stated meanings, and Nu is a nucleofugic leaving group, with a 3-azabicyclo-[3.2.0] heptane derivative of the formula III

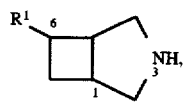 III where $R^1$ is naphthyl or phenanthryl which is unsubstituted, mono- or disubstituted by halogen atoms, and converting the resulting compounds where appropriate into their salts with physiologically suitable acids.

Suitable and preferred nucleofugic leaving groups Nu are halogen atoms, in particular bromine or chlorine.

The reaction is expediently carried out in the presence of an inert base such as triethylamine or potassium carbonate to trap acid, in an inert solvent such as a cyclic saturated ether, in particular tetrahydrofuran or dioxane, or an aromatic hydrocarbon such as toluene or xylene.

The reaction normally takes place at from 20° to 150° C., and is generally complete within 1–10 hours.

The compounds of the formula I according to the invention can be purified either by recrystallization from conventional organic solvents, preferably from a lower alcohol such as ethanol, or by column chromatography.

Racemates can be fractionated to the enantiomers in a simple way by classical resolution using optically active carboxylic acids, eg. tartaric acid derivatives, in an inert solvent, eg. lower alcohols.

The free 3-azabicyclo[3.2.0]heptane derivates of the formula I can be converted in a conventional way into the salt of a pharmacologically suitable acid, preferably by treating a solution with one equivalent of the appropriate acid. Examples of pharmaceutically suitable acids are hydrochloric acid, phosphoric acid, sulfuric acid, methanesulfonic acid, sulfamic acid, maleic acid, fumaric acid, oxalic acid, tartaric acid or citric acid.

The compounds according to the invention have valuable pharmacological properties. They can be used as neuroleptics (especially atypical), antidepressants, sedatives, hypnotics, CNS protectives or muscle relaxants. A compound according to the invention may display several of said types of action in combination. The pharmacological action is demonstrated both in vivo and in vitro, it being possible to characterize the substances in particular by the affinity, which is in some cases very high and selective, for receptor subtypes, especially dopamine $D_4$ receptors.

The following methods have been used for the in vivo characterization:

a) Influence on orientation motility

In a new environment, mice show an exploratory behavior manifested by increased motor activity. This motor activity is measured in light barrier cages for 0–30 min after the animals (NMRI mice, female) have been placed in the cage. ED50: dose which reduces the motor activity by 50% compared with placebo-treated controls.

b) Apomorphine antagonism

Female NMRI mice receive 1.21 mg/kg apomorphine s.c. At this dose, apomorphine leads to motor activation manifested by a permanent climbing when the animals are kept in wire mesh cages. The climbing is scored every 2 min for 30 min:

0: animal has four paws on the floor
1: animal has two paws on the wire
2: animal has four paws on the wire (is climbing).

The climbing behavior can be inhibited by pretreatment with antipsychotics.

ED50: dose which inhibits the climbing activity of the animals by 50% compared with placebo-treated controls.

c) L-5-HTP antagonism

Female Sprague-Dawley rats receive L-5-HTP in a dose of 316 mg/kg i.p. The animals then develop an agitation syndrome, of which the symptoms of forepaw treading and
tremor are scored (0=absent, 1=moderate, 2=pronounced) every 10 min in the time from 20 to 60 min after administration of L-5-HTP. The average score after administration of L-5-HTP is 17. The test substances are given p.o. 60 min before L-5-HTP. The ED50 is calculated as the dose reducing the control score by 50% on average.

The listed methods are suitable for characterizing substances as antipsychotics. A serotinin-antagonistic effect can be revealed by the inhibition of the L-5-HTP syndrome, and this type of effect is characteristic of atypical neuroleptics.

The novel substances show a good effect in these tests.

The invention accordingly also relates to a therapeutic composition having a content of a compound of the formula I or its pharmacologically suitable acid addition salt as active ingredient in addition to conventional excipients and diluents, and to the use of the novel compounds for controlling diseases.

The compounds according to the invention can be administered orally or parenterally, intravenously or intermuscularly, in a conventional way.

The dosage depends on the age, condition and weight of the patient and on the mode of administration. The daily dose of active ingredient is, as a rule, about 1–100 mg/kg of body weight on oral administration and 0.1–10 mg/kg of body weight on parenteral administration.

The novel compounds can be used in conventional solid or liquid pharmaceutical forms, eg. as uncoated or (film-) coated tablets, capsules, powders, granules, suppositories, solutions, ointments, creams or sprays. These are produced in a conventional way. The active ingredients can for this purpose be processed with conventional pharmaceutical aids such as tablet binders, bulking agents, preservatives, tablet disintegrants, flow regulators, plasticizers, wetting agents, dispersants, emulsifiers, solvents, release-slowing agents, antioxidants and/or propellent gases (cf. H. Sucker et. al: Pharmazeutische Technologie, Thieme-Verlag, Stuttgart, 1978). The administration forms obtained in this way normally contain from 1 to 99% by weight of active ingredient.

The substances of the formula II required as starting materials for synthesizing the novel compounds are known.

The substances of the formula III can be prepared by subjecting an amine of the formula IV

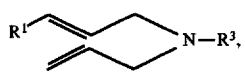
IV where $R^1$ has the abovementioned meanings, and $R^6$ is hydrogen, acetyl, benzyl or trifluoroacetyl, to a photochemical [2+2] cyclo-addition and then, where appropriate, eliminating an acyl or benzyl group.

The photoreaction takes place while in an inert solvent, preferably acetone, at from 20° to 80° C. A particularly suitable light source is a high-pressure mercury lamp. It may be advantageous to carry out the photocycloaddition in a quartz apparatus under a nitrogen atmosphere with or without the addition of about 1 mole of hydrochloric acid per mole of amine.

The photocycloaddition is in most cases highly diastereoselective to give the bicyclic compounds III with the exo configuration with respect to $R^1$:

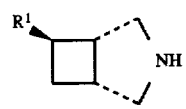

The two enantiomers can be isolated pure by racemate resolution, eg. using optically active tartaric acid derivatives.

An acyl radical ($R^6$) is expediently eliminated by conventional hydrolysis methods. A similar statement applies to the elimination of the benzyl radical.

The amines of the formula IV are disclosed in the literature or can be prepared by either reacting an aldehyde $R^1$—CHO with vinyl-magnesium chloride to give the allyl alcohol V

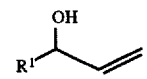
V then rearranging with hydrogen chloride to give the allyl chloride VI

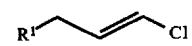
VI and finally reacting with the appropriate allylamine VII

 VII or subjecting a cinnamaldehyde VIII

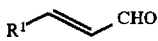 VIII directly to reductive amination with the allylamine VII.

The following examples illustrate the invention:

A Preparation of the starting materials aa) 1-(1-Naphthyl)allyl alcohol 277 ml (360 mmol) of a 1.3M solution of vinylmagnesium chloride in tetrahydrofuran were introduced under nitrogen into a 2 l stirred flask. Subsequently, while stirring under nitrogen at 30°–35° C., a solution of 50 g (320 mmol) of 1-naphthaldehyde dissolved in 250 ml of tetrahydrofuran was added over the course of 60 min. The mixture was then stirred at room temperature under nitrogen for 4.5 h. 90 ml of saturated ammonium chloride solution were then added while stirring and cooling with ice, the mixture was filtered with suction and the residue on the filter was washed three times with 150 ml of tetrahydrofuran. The filtrates were combined, dried with sodium sulfate and concentrated. 58.3 g (99%) of crude product were obtained in the form of a brown oil.

ab) 3-(1-Naphthyl)allyl chloride 58.3 g (317 mmol) of 1-(1-naphthyl)allyl alcohol were dissolved in 400 ml of dichloromethane with stirring. Hydrogen chloride was then passed in to saturation, during which the temperature rose to 37° C. The mixture was then stirred for 1 h. The organic phase was washed with 200 ml of ice-cold water, dried over sodium sulfate and concentrated. 59.2 g (92%) of brownish solid were obtained.

ac) N-Allyl-N-[3-(1-naphthyl)allyl]amine 59.2 g (0.29 mol) of 3-(1-naphthyl)allyl chloride dissolved in 250 ml of toluene were added over the course of 1 h to 167 g (2.9 mol) of allylamine under reflux. The mixture was then refluxed for 2 h. The solution was subsequently concentrated, the residue was taken up in 250 ml of water, and the pH was adjusted to 12 with 50% strength sodium hydroxide solution. The aqueous phase was extracted with dichloromethane, and the organic phase was dried over sodium sulfate and concentrated. Yield: 67.6 g (97%) of dark brown oil.

ad) exo-6-(1-Naphthyl)-3-azabicyclo[3.2.0]heptane 50.0 g (193 mmol) of N-allyl-N-[3-(1-naphthyl)allyl] ammonium chloride were dissolved in 1600 ml of acetone, and 210 ml of 10% strength hydrochloric acid were added. The clear yellow solution was irradiated under nitrogen using a 700 watt high-pressure mercury lamp in a quartz apparatus at room temperature for 4 h. The solution was then concentrated, the residue was taken up with water, and the pH was adjusted to 12 with 50% strength sodium hydroxide solution. The mixture was then stirred for 30 min and extracted twice with tert-butyl methyl ether. The combined organic phases were dried over sodium sulfate and concentrated.

The dark brown oily residue (43.2 g) was dissolved in 150 ml of isopropanol, and 25.5 g (220 mmol) of maleic acid dissolved in 220 ml of isopropanol were added. The precipitated maleate was filtered off with suction, washed with isopropanol and dried in a vacuum oven at 40° C. overnight. Yield: 43.9 g (67%) of colorless powder, melting point 162°–164° C. (maleate).

The following substances can be prepared in a similar way:

ae) exo-6-(2-naphthyl)-3-azabicyclo[3.2.0]heptane, melting point 145°–147° C. (maleate)

af) exo-6-(5-chloro-1-naphthyl)-3-azabicyclo[3.2.0] heptane.

ag) exo-6-(9-phenanthryl)-3-azabicyclo[3.2.0]heptane.

ah) exo-6-(6-chloro-2-naphthyl)-3-azabicyclo[3.2.0] heptane, melting point 164°–165° C.

B) Preparation of the final products

EXAMPLE 1

N-[2-(exo-6-(1-Naphthyl)-3-azabicyclo[3.2.0] heptan-3-yl)ethyl]benzamide 6.6 g (35.2 inmol) of N-(2-chloroethyl)benzamide and 2.5 g (18.1 mmol) of finely powdered potassium carbonate and 0.5 g of potassium iodide were added to 4.0 g (17.8 mmol) of exo-6-(1-naphthyl)-3-azabicyclo[3.2.0]heptane in 70 ml of toluene, and the mixture was refluxed for 6 h. After cooling and concentration in a rotary evaporator, the residue was partitioned between methylene chloride and water. The aqueous phase was then extracted twice with methylene chloride, and the organic phase was dried with sodium sulfate and concentrated. The crude product (8.9 g) was purified by column chromatography (silica gel, mobile phase dichloromethane/methanol 96/4). The free base (3.0 g) was dissolved in 100 ml of tert-butyl methyl ether, and excess ethereal hydrochloric acid was added while cooling in ice. The precipitated hydrochloride was filtered off with suction under nitrogen, washed with a large amount of tert-butyl methyl ether and dried on the funnel under a stream of nitrogen. 2.6 g (35%) of product were isolated as hydrochloride, melting point 184°–186° C.

The following can be prepared in a similar way:

2. N-[2-(exo-6-(2-Naphthyl)-3-azabicyclo[3.2.0]heptan-3-yl)ethyl]benzamide, melting point 233°–235° C. (hydrochloride).

3. N-[2-(exo-6-(5-Chloro-1-naphthyl)-3-azabicyclo-[3.2.0]heptan-3-yl)ethyl]benzamide.

4. 3-[2-(1-Naphthyl)ethyl]-exo-6-(1-naphthyl)-3-azabicyclo-[3.2.0]heptane, melting point 227°–229° C. (hydrochloride).

5. 3-[2-(1-Naphthyl)ethyl]-exo-6-(2-naphthyl)-3-azabicyclo[3.2.0]heptane, melting point 208°–210° C. (hydrochloride).

6. 1-[2-(exo-6-(1-Naphthyl)-3-azabicyclo[3.2.0]heptan-3-yl)ethyl]-1H-benzo[cd]indol-2-one, melting point 174°–176° C. (hydrochloride).

7. 1-[2-(exo-6-(2-Naphthyl)-3-azabicyclo[3.2.0]heptan-3-yl)-ethyl]-1H-benzo[cd]indol-2-one, melting point 258°–260° C. (hydrochloride).

8. 3,3-Dimethyl-1-[2-(exo-6-(1-naphthyl)-3-azabicyclo-[3.2.0]heptan-3-yl)ethyl]-1,3-dihydroindol-2-one.

9. 3,3-Dimethyl-1-[2-(exo-6-(2-naphthyl)-3-azabicyclo-[3.2.0]heptan-3-yl)ethyl]-1,3-dihydroindol-2-one, melting point 124°–125° C., 10. 3,3-Dimethyl-1-[2-(exo-6-(6-chloro-2-naphthyl)-3-azabicyclo[3.2.0]heptan-3-yl)ethyl]-1,3-dihydroindol-2-one.

11. 5-Chloro-N-[2-(exo-6-(1-naphthyl)-3-azabicyclo-[3.2.0]-heptan-3-yl)ethyl]-2-thiophenecarboxamide.

12. 5-Chloro-N-[2-(exo-6-(2-naphthyl)-3-azabicyclo[3.2.0]-heptan-3-yl)ethyl]-2-thiophenecarboxamide.

13. N-[2-(exo-6-(1-Naphthyl)-3-azabicyclo[3.2.0]heptan-3-yl)-ethyl]-4-fluorobenzamide.
14. N-[2-(exo-6-(2-Naphthyl)-3-azabicyclo[3.2.0]heptan-3-yl)-ethyl]-4-nitrobenzamide.
15. N-[2-(exo-6-(6-Chloro-2-naphthyl)-3-azabicyclo[3.2.0]-heptan-3-yl)ethyl]benzamide, melting point 102°–104° C..
16. N-[2-(exo-6-(1-Naphthyl)-3-azabicyclo[3.2.0]heptan-3-yl)-ethyl]-4-methoxybenzamide.
17. N-[2-(exo-6-(2-Naphthyl)-3-azabicyclo[3.2.0]heptan-3-yl)-ethyl]-4-hydroxybenzamide.
18. N-[2-(exo-6-(1-Naphthyl)-3-azabicyclo[3.2.0]heptan-3-yl)-ethyl]-3,4-dichlorobenzamide.
19. N-[2-(exo-6-(1-Naphthyl)-3-azabicyclo[3.2.0]heptan-3-yl)-ethyl]naphthalene-1-carboxamide.
20. N-[2-(exo-6-(2-Naphthyl)-3-azabicyclo[3.2.0]heptan-3-yl)-ethyl]naphthalene-1-carboxamide.
21. N-[2-(exo-6-(9-Phenanthryl)-3-azabicyclo[3.2.0]heptan-3-yl)ethyl]benzamide, melting point 110°–112° C. (hydrochloride).
22. 1-[2-(exo-6-(6-Chloro-2-naphthyl)-3-azabicyclo-[3.2.0]heptan-3-yl)ethyl]-1H-benzo[cd]indol-2-one.
23. 1-[2-(exo-6-(9-Phenanthryl)-3-azabicyclo-[3.2.0]heptan-3-yl)ethyl]-1H-benzo[cd]indol-2-one.
24. N-[2-(exo-6-(1-Naphthyl)-3-azabicyclo[3.2.0]heptan-3-yl)-ethyl]isoindolinone.
25. N-[2-(exo-6-(2-Naphthyl)-3-azabicyclo[3.2.0]heptan-3-yl)-ethyl]isoindolinone.

We claim:

1. An N-substituted 3-azabicyclo[3.2.0]-heptane derivate of the formula I

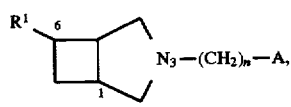

where

R$^1$ is naphthyl or phenanthryl which is unsubstituted, mono- or disubstituted by halogen atoms, n is 1, 2, 3 or 4, A is

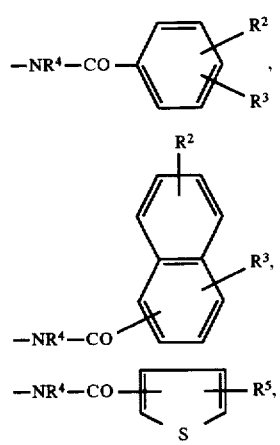

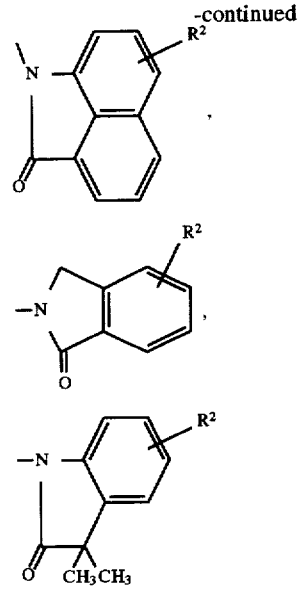

or naphthyl which is unsubstituted or halogen-substituted,

R$^2$ is hydrogen, hydroxyl, C$_1$–C$_4$-alkyl, nitro or methoxy, or fluorine, chlorine, bromine or iodine, R$^3$ is hydrogen, fluorine or chlorine, R$^4$ is hydrogen or methyl, and R$^5$ is hydrogen or chlorine, and the salts thereof with physiologically tolerated acids.

2. A method for treating psychoses which comprises administering an effective dose of a compound of the formula I as defined in claim 1 to patients.

3. A process for preparing compounds of the formula I

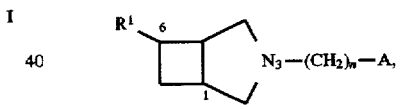

where

R$^1$ is naphthyl or phenanthryl which is unsubstituted, mono- or disubstituted by halogen atoms, n is 1, 2, 3 or 4, A is

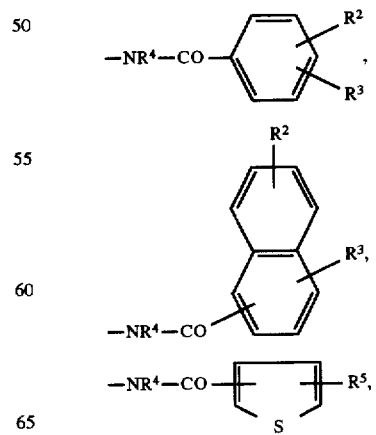

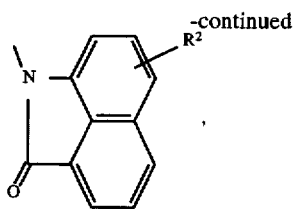

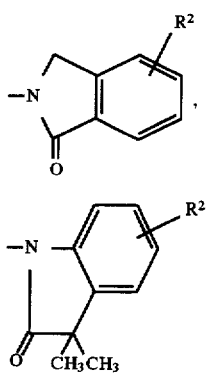

or naphthyl which is unsubstituted or halogen-substituted, $R^2$ is hydrogen, hydroxyl, $C_1$–$C_4$-alkyl, nitro or methoxy, or fluorine, chlorine, bromine or iodine, $R^3$ is hydrogen, fluorine or chlorine, $R^4$ is hydrogen or methyl, and $R^5$ is hydrogen or chlorine, and the salts thereof with physiologically tolerated acids, which process comprises reacting a compound of the formula II

where A and n have the stated meanings, and Nu is a nucleofugic leaving group, with a 3-azabicyclo-(3.2.0) heptane derivative of the formula III

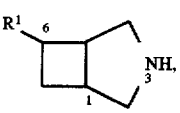

where $R^1$ has the stated meaning, and optionally converting the resulting compounds where appropriate into their salts with physiologically suitable acids.

* * * * *